United States Patent [19]

Ray

[11] Patent Number: 5,058,178
[45] Date of Patent: Oct. 15, 1991

[54] METHOD AND APPARATUS FOR INSPECTION OF SPECULAR, THREE-DIMENSIONAL FEATURES

[75] Inventor: Rajarshi Ray, Princeton, N.J.

[73] Assignee: AT&T Bell Laboratories, Murray Hill, N.Y.

[21] Appl. No.: 454,210

[22] Filed: Dec. 21, 1989

[51] Int. Cl.[5] .......................... G06K 9/00; G06K 9/03
[52] U.S. Cl. ........................................ 382/8; 358/106; 356/237
[58] Field of Search ................... 358/106; 356/237; 382/8

[56] References Cited

U.S. PATENT DOCUMENTS

| | | | |
|---|---|---|---|
| 4,441,025 | 4/1984 | Berkin et al. | 382/8 |
| 4,677,473 | 6/1987 | Okamito et al. | 382/8 |
| 4,688,939 | 8/1987 | Ray | 356/237 |
| 4,692,943 | 9/1987 | Pietzsch et al. | 382/8 |
| 4,696,047 | 9/1987 | Christian et al. | 382/8 |

*Primary Examiner*—Leo H. Boudreau
*Assistant Examiner*—David Fox
*Attorney, Agent, or Firm*—Robert B. Levy

[57] ABSTRACT

Defective or missing solder bumps (18) on a surface (13) of an article (10) such as a chip carrier are detected by first illuminating the surface with dark field illumination. Next, the image of the surface of the article is captured, typically by a television camera (30). The captured image is processed to detect defects by first creating a window (57) in the image about each group of solder bumps and then creating a bounding box (58) about each bump in each window. Each of a set of attributes, including: the number, size and location of the windows, the size location and number of boxes in each window, and the dimensions, shape and brightness of the image in each box, is measured. The value of each attribute is compared to a reference value, representing the value of the attribute when no defects are present. If the attribute differs by more than a predetermined tolerance for its reference value, than a particular defect is prevent. Verification of certain defects may be accomplished by repeating the above-described process using bright field illumination.

13 Claims, 5 Drawing Sheets

| SIDE VIEW OF SOLDER BUMP 18 | TOP VIEW OF DARK FIELD ILLUMINATION | TOP VIEW OF BRIGHT FIELD ILLUMINATION |
|---|---|---|
|  |  |  |
| | GOOD BUMP | |
|  |  |  |
| | POOR WETTING | |
|  |  |  |
| | MISSING | |
|  |  |  |
| | OVERFLOW | |
|  |  |  |
| | BRIDGING | |
|  |  |  |
| | SQUASHED OR UPRIGHT BUMP | |
|  |  |  |
| | CONCAVE BUMP | |
|  |  |  |
| | GRAINY BUMP/ CONTAMINANTS/ COLD SOLDER | |
|  |  |  |
| | HOLE OR CAVITIES ON BUMP SURFACE | |

METHOD AND APPARATUS FOR INSPECTION OF SPECULAR, THREE-DIMENSIONAL FEATURES

TECHNICAL FIELD

This invention relates generally to a method and apparatus for detecting missing or defective specular, three-dimensional features, such as solder bumps, on the surface of an article.

BACKGROUND OF THE INVENTION

Soldering remains the method of choice for bonding an electrical component to the surface of a substrate, such as a printed circuit board. Different processes are employed to bond different types of components. For example, a leadless surface-mounted component (e.g., a chip carrier) having metal pads on its exterior for bonding to metallized areas on a circuit board, is attached to the board by first depositing a volume (i.e., a "bump") of solder on each pad. Following application of the solder bumps, the chip carrier is then adhered to the circuit board so each solder bump is in aligned contact with a corresponding metallized area on the surface of the board. Finally, the chip carrier and the circuit board are heated to reflow the solder bumps so that the bumps bond the pads on the chip carrier to the metallized areas on the board.

The "solder bump" bonding process described above may also be used to attach each bond site on a semiconductor chip to a corresponding bond site on the surface of a semiconductor wafer. First, solder bumps are applied to the bond sites on the wafer and on the chip. The chip is then placed with its solder bumps in aligned contact with the solder bumps on the wafer, and thereafter, the solder bumps are reflowed to form a solid mechanical and electrical bond between the chip and the wafer.

The overall reliability of the solder bonds created by the solder bump process is adversely affected by missing and defective bumps. For example, if a solder bump is missing, or is of an insufficient height, then no electrical connection is made between the corresponding pad on the chip carrier and the circuit board or between the bond site on the semiconductor chip and on the wafer. Bridging between two adjacent solder bumps creates a unwanted short circuit. Solder bumps which are spaced too close together may later bridge during reflow, also giving rise to an unwanted short circuit.

Other types of undesirable defects include poor wetting caused by a pad or bond site which is untinned prior to application of the solder bump. This type of defect generally reduces the strength of the resultant solder bond. Defects such as "cold" (i.e., grainy) solder bumps, and bumps which have surface deformations (e.g., holes, pits or cavities) may cause an otherwise good solder joint to fail prematurely. Solder spatter or debris, characterized by the adhesion of isolated globules of solder to the chip carrier, or to the semiconductor chip or wafer following application of the solder bumps, is undesirable since it may lead to short circuits.

In an effort to detect defects of the type described above, I developed a solder bump inspection system which is described in U.S. Pat. No. 4,688,939, issued on Aug. 25, 1987, to AT&T Technologies Inc., and which is also described in my article "Automated Visual Inspection of Solder Bumps," published in the AT&T Technical Journal, March/April 1988, Vol. 67, Issue 2, at pages 47-60. The solder bump inspection system described in my patent and my article (both incorporated by reference herein) comprises a television camera trained on an electronic component undergoing inspection such that the optical axis of the camera is substantially normal to the surface of the component. A ring light illuminates the article's surface with "dark field" illumination by directing light at an angle with the surface from all sides. When the light is directed at the surface in this manner, only the light striking the curved surface of a specular, three-dimensional feature, such as solder bump, is reflected into the television camera. A machine vision processor processes the output signal of the camera to provide a one-dimensional plot of the cumulative intensity of the light reflected from the surface as a function of the lateral distance therealong.

From such a plot of the reflectance intensity (known as a profile), my previous solder bump inspection system can reveal defects such as missing, bridged, and excessive bumps. Further, by re-positioning of the ring lamp to provide "bright field" illumination (i.e. light striking the surface of the article substantially normal to its plane), poor wetting can also be detected. As useful as my previous solder bump inspection system is, there are certain defects which it cannot readily inspect. For example, subtle defects such as cold ("grainy) solder, near shorts, solder spatter, squashed bumps and bumps whose surface topography is deformed, i.e., the bumps are concave, or their surfaces contain pits, holes or cavities, cannot be easily detected by my previous system.

Thus, there is a need for an improved technique for inspecting solder bumps in order to detect as many different types of defects as possible.

SUMMARY OF THE INVENTION

Briefly, in accordance with a preferred embodiment of the invention, a technique is provided for inspecting a surface of an article to detect missing and defective specular, three-dimensional topographical features, such as solder bumps. The inspection is carried out by first illuminating the surface of the article with dark-field illumination. Next, the image of the surface is captured by an image-acquisition device, such as a television camera, whose optical axis is substantially normal to the surface of the article. The captured image is then thresholded so that those portions of the image whose reflectance intensity is below a predetermined value are made dark. In this way, the bright features which remain in the image should correspond only to the solder bumps (and any solder spatter) on the surface of the article. These bight features in the image constitute a projection of the three-dimensional surface features on the image plane of the television camera. Following thresholding of the image, a window is created around each group of bright features (solder bumps) in the image, and a bounding box is created about each bright area in each window. Next, the values of certain attributes associated with each window (i.e., its location, size and the number of bounding boxes therein) as well as the values of certain attributes of each box (i.e., its location, size and spacing from its closest neighbor), are measured. Also the values of certain attributes associated with the bright area inside each bounding box (i.e., its dimensions, shape and brightness) are also measured. The measured value of each attribute is then compared to a reference value, representing the expected value of the attribute when no defect is present. A deviation in the value of each attribute from its corresponding reference value by more than a predetermined tolerance is indicative of a particular defect.

In accordance with another aspect of the invention, particular defects (i.e., poor wetting, squashed bumps, and near shorts) may be verified by first illuminating the surface of the article with bright field illumination instead of dark field illumination. The image of the surface is once again captured and thresholded. Windows and bounding boxes are established within the image in the same manner as during dark field illumination. Each of a set of predetermined attributes associated with the windows and boxes and the bright features in the boxes is measured, the attributes being the same as those measured under dark field illumination. The measured values are compared against a set of reference values, each corresponding to the value of the particular attribute under bright field illumination when no defect is present. If the measured value deviates from the corresponding value by more than a predetermined tolerance, then, the corresponding defect identified during dark field illumination will be verified under bright field illumination.

DETAILED DESCRIPTION

Figure 1:
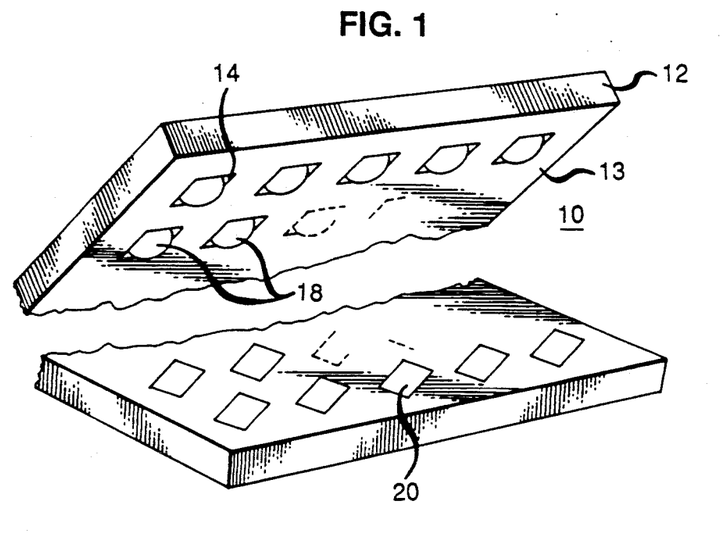
FIG. 1 is a perspective view of a prior art chip carrier having solder bumps applied to metallized pads on a planar, exterior surface the chip carrier.

FIG. 1 is a perspective view of a prior art leadless chip carrier 10 which is comprised of a semiconductor chip (not shown) housed within a prismatic package (enclosure) 12. The package 12 has a generally planar exterior surface 13 on which is arranged a pattern of flat metal pads 14, each pad being electrically coupled to the chip inside the package. In a preferred embodiment, the pads 14 are arranged in four separate rows which form the perimeter of a square. Other patterns may be found on different types of chip carriers.

Typically, the chip carrier 10 is bonded to a substrate 16, such as a circuit board, by solder which is usually first deposited on each pad 14 in the form of a generally spherical bump 18. Thereafter, the chip carrier 10 is adhered to the circuit board 16 so that each solder bump 18 is in contact with a separate metallized area 20 on the board. The chip carrier 10 and the circuit board 16 are then heated to reflow the bumps 18 on the pads 14 to bond them to the metallized areas 20 on the board. Rather than apply the solder bumps 18 to the chip carrier 10, the solder bumps could be applied to metallized areas 20 on the circuit board to achieve the same result.

The reliability of the solder bond between each pad 14 on the chip carrier 10 and each metallized area 20 on the circuit board 16 is dependent on the presence and quality of the solder bump 18 adhered to the pad (or, alternatively, to the metallized area). If the bump 18 is missing or is too short, then no electrical contact will be made between the pad 14 and the corresponding metallized area 20. A solder bump 18 which has bridged with an adjacent bump creates an unwanted short circuit. Poor wetting of the bump 18 to its pad 14 decreases the strength of the solder joint formed between the pad and the metallized area 20, and may lead to premature failure of the solder joint. Premature failure may also occur if the bump 18 is "cold" (e.g., grainy) or has surface deformations, such as holes, pits or cavities.

Figure 2:
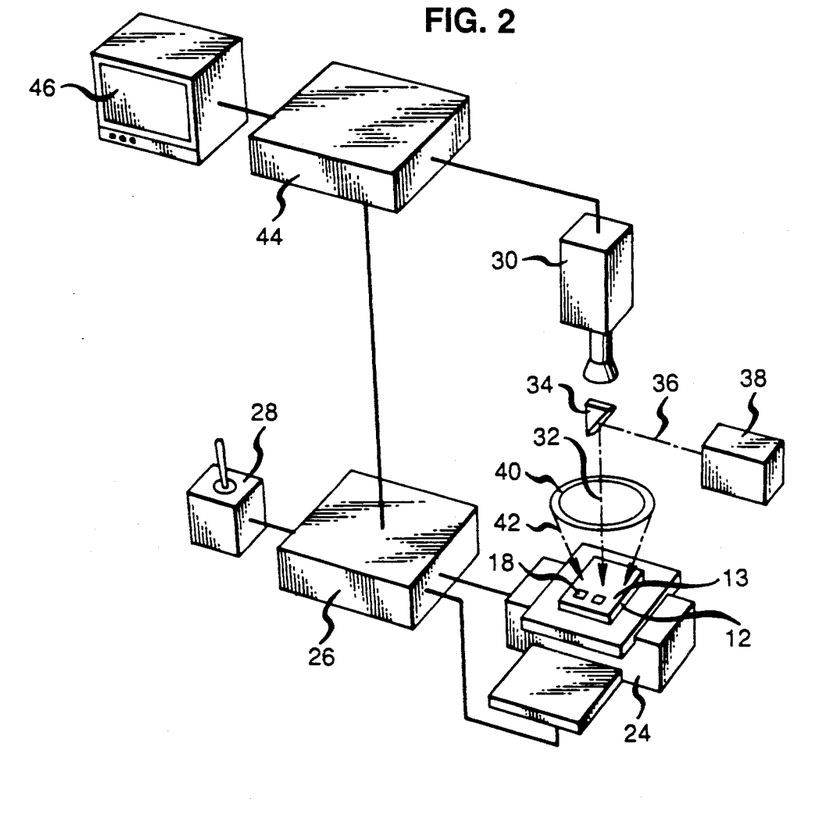
FIG. 2 is a schematic illustration of a system, in accordance with the invention, for inspecting the solder bumps on the chip carrier of FIG. 1 to detect if any are missing or defective.

Referring to FIG. 2, there is shown a system 22, in accordance with the present invention, for inspecting an article, such as the chip carrier 10 of FIG. 1, to detect missing or defective solder bumps 18 and defects such as solder spatter. The system 22 comprises a stage 24 for supporting the chip carrier 10 to be inspected. Suitable means (not shown) such as a robot or the like, may be provided for transporting the chip carrier 10 to and from the stage 24. In practice, the stage 24 is motorized for movement along both x and y axes lying in the same plane. A stage controller 26 serves to control the stage 24. Manual control of the stage 24 may be achieved by manipulating a joystick 28 coupled to the stage controller 26.

An image-acquisition device 30, in the form of a television camera, is trained on the stage 24 such that the camera has its optical axis 32 normal to the surface 13 of the chip carrier 10 placed on the stage. Interposed between the television camera 30 and the stage 24 is a beam splitter 34 which is positioned so that the optical axis 32 of the camera passes vertically through the beam splitter. A generally collimated light beam 36 from a light source 38 is directed into the beam splitter 34 at a right angle to the optical axis 32 of the camera. Upon entering the beam splitter 34, the beam 36 is reflected and refracted so as to be coaxial with the optical axis 32 and thus, will strike the surface 13 of the chip carrier 10 normal to its plane. A ring light 40 circumscribes the optical axis 32 of the television camera 30 and serves to illuminate the surface 13 with light, represented by a set of beams 42, directed at an acute angle to the surface from all sides thereof.

The ring light 40 serves to illuminate the surface of the chip carrier 10 with "dark field" illumination whereas the light source 38 provides "bright field" illumination. A better understanding of bright field and dark field illumination may be had by reference to FIG. 3 which shows a side-view of the chip carrier 10. Dark field illumination is achieved with the light beams 42 being directed at the surface 13 at an acute angle so as to be reflected vertically upward upon striking a specular, generally rounded, three-dimensional feature, such as a solder bump 18. Were one of the beams 42 to strike a generally planar reflective surface, such as an unbumped pad 14 (i.e., a pad having no solder bump 18), then the beam would be reflected away from the television camera 30 of FIG. 2.

Figure 3:
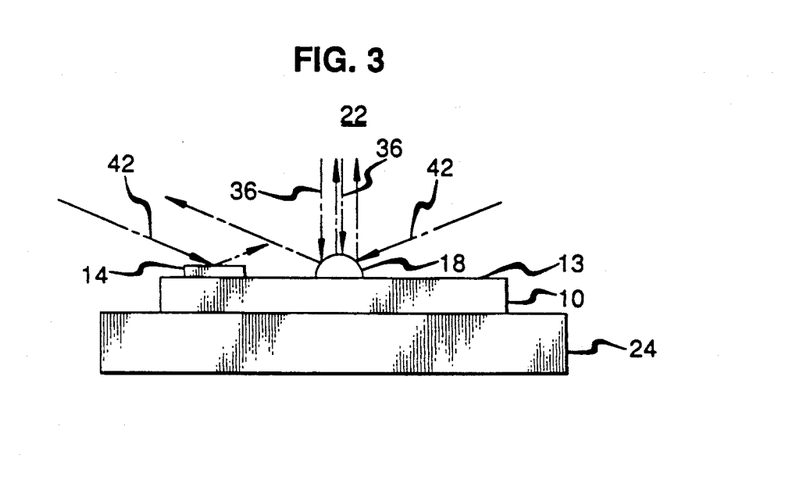
FIG. 3 is side view of the chip carrier of FIG. 1 showing the manner in which light is reflected from a solder bump on its surface under dark field illumination and under bright field illumination.

In contrast to dark field illumination, bright field illumination is achieved by directing the beam 36 at the surface 13 of the chip carrier 10 normal to its plane. When the beam 32 strikes a solder bump 18, only the light which strikes a generally planar portion of the solder bump 18 (i.e., its tip) will be reflected normally upward and into the television camera 30 of FIG. 2. The portion of the beam 32 striking the rounded surface of the solder bump 18 will be scattered at an acute angle with the plane of the surface 13 and thus will be scattered away from the television camera 30 of FIG. 2.

Figure 4:
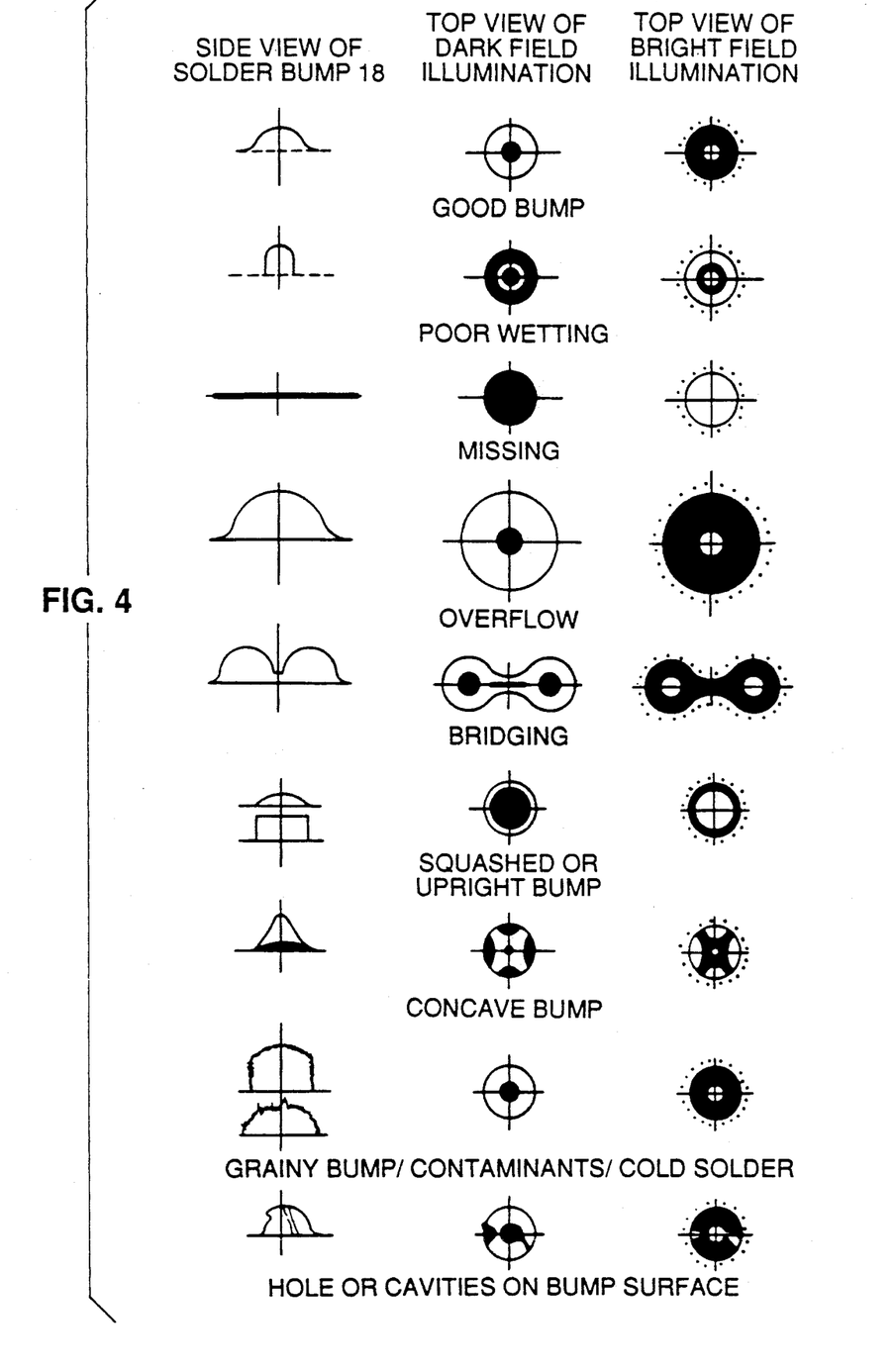
FIG. 4 is a chart showing a side view, a top view under dark field illumination, and a top view under bright field illumination, respectively, of the chip carrier of FIG. 1 when the chip carrier has no defects, and when each of several different types of defects is present.

Referring to FIG. 4, there is shown a chart depicting a side view, a top view under dark field illumination, and a top view under bright field illumination, respectively, of a solder bump 18 which is good, as well as each of a plurality of bumps having separate defects. As may be seen in FIG. 4, a good solder bump 18, when viewed from the top under dark field illumination, appears as a bright annulus whose center is dark. Conversely, under bright field illumination, a good solder bump 18 will appear as a dark annulus whose center is bright. Concentric with the dark annulus which represents the solder bump 18 under bright field illumination is a ring formed of small dark spots which represents the texture of the planar background surrounding the bump. The bright field images seen in the chart in FIG. 4 have been simplified for purposes of illustration since, in practice, they are very feature rich in their appearance.

When the solder bump 18 is defective, its image observed both under bright field and dark field illumination will be different from the image when the bump is good. How the image differs depends on the nature of the defect. For example, if the solder bump 18 is squashed, then the inner diameter of the bright and dark annulus which appears under dark field and bright field illumination, respectively, will appear larger than when the bump is good. Conversely, if the bump 18 is too large (i.e., an overflow occurred), then the outer diameter of the bright and dark annulus seen under dark and bright field illumination, respectively, will be larger than if the bump were good.

Referring to FIG. 2, the camera 30 has its output coupled to a machine vision processor 44 which, in a preferred embodiment, comprises a model P256 vision system manufactured by Industrial Robomation Inc. (IRI) of Carlsbad, Calif. The preferred embodiment of the vision processor 44 typically contains a microprocessor (not shown) which serves to process the output of the television camera 30 to establish whether any of the solder bumps 18 are missing or otherwise defective. In addition to processing the output signal of the television camera 30, the vision processor 44 also serves as a host computer to the stage controller 26 to control its operation. A video monitor 46 is coupled to the vision processor 44 to display its output.

Figure 5:
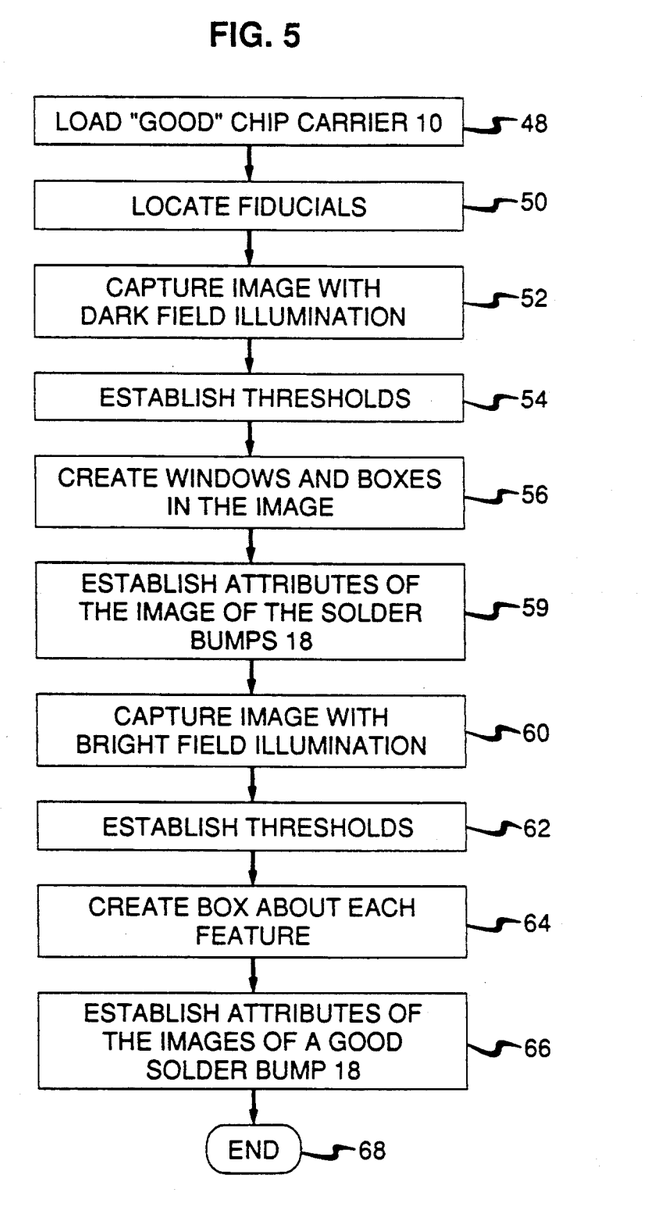
FIG. 5 is a flowchart diagram of a program executed by the system of FIG. 2 to train itself to inspect the chip carrier of FIG. 1.

In accordance with the invention, the vision processor 44 detects solder spatter as well as missing or defective solder bumps 18 by comparing the value of certain attributes of the chip carrier image to the corresponding attributes of the image of a good (non-defective) chip carrier 10. In order for the vision processor 44 to make such a comparison, the processor must be "trained", that is to say, the values of the particular attributes for a good chip carrier 10 must be established. Referring to FIG. 5, there is shown a flowchart representation of a program executed by the vision processor 44 prior to the actual inspection of the chip carrier 10 to establish the value of the attributes of a good chip carrier which will be used for comparison purposes.

The first step (step 48) in the program of FIG. 5 is load a "good" chip carrier 10 (see FIGS. 1 and 2) onto the stage 24 of FIG. 2. A good chip carrier 10 is one which has at least one defect-free solder bump 18 (see FIGS. 1 and 2) and preferably, all of its solder bumps being defect free. Once the chip carrier 10 has been loaded, then the next step (step 50) is to locate each of a set of reference fiducials (not shown) provided on the surface 13 of FIG. 1 with the vision processor 44. Typically, the entire image of the chip carrier 10 will usually appear within the field of view of the television camera 30. However, in instances where the chip carrier 10 is too large so only a portion of its image is within the field of the television camera 30, it may be necessary to manually jog the stage 24 of FIG. 2 so each fiducial can be situated within the field of view of the television camera 30. Once the fiducials are located, then the location of each of the pads 14 (see FIG. 1), and hence the solder bumps 18, can be found since the distance of each pad from the fiducial is known a priori from the design of the chip carrier 10.

Following step 50, step 52 of FIG. 5 is executed and the image of the surface 15 of the chip carrier 10 under dark field illumination is captured. Depending on the site of the chip carrier 10, it may be necessary to capture portions of the chip carrier image separately. To carry out step 52, the ring lamp 40 is energized while the light source 38 is extinguished so that only the light beams 42 strike the chip carrier surface 13. Once the image of the chip carrier surface 13 has been captured, a threshold gray level is established for the captured image (step 54). The threshold gray level represents a certain image brightness level which is typically set so that those bright portions of the image which correspond to the solder bumps 18 (and any solder spatter) have a brightness level exceeding the threshold. As will be described later, the threshold gray level is employed during subsequent image processing to darken the dull portions of the image.

Figure 6:
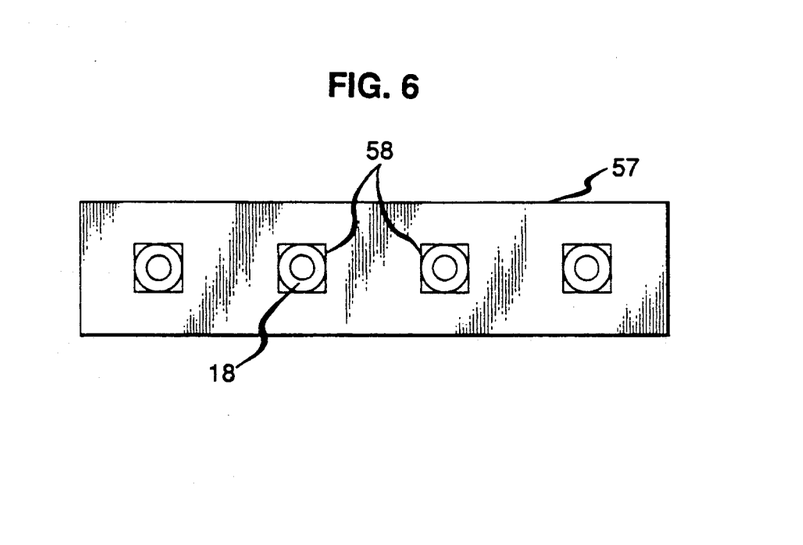
FIG. 6 is a pictorial representation of a portion of the image of the chip carrier of FIG. 1 captured during execution of the training routine of FIG. 5.

Once step 54 has been completed, step 56 is executed, and a set of windows 57 and boxes 58 (see FIG. 6) are created within the image. During step 56, a window 57 is created about each row of the bumps 18 as seen in FIG. 6. A bounding box 58 is established about the image of each solder bump 18 within each window 57 using connectivity analysis techniques. The location of the windows 57, their size, as well as the number, location and size of boxes 58 within each window, are then recorded during this step. The IRI model P256 vision processor, which comprises the vision processor 44, is capable of being programmed to create the windows 57 and the bounding boxes 58 in the captured image (by examining the connectivity of the bright images) as well as to measure the above-described attributes of the windows and boxes.

After creation of the windows 57 and boxes 58 of FIG. 6, then step 59 of FIG. 5 is executed, and a set of predetermined attributes in the image of at least one good solder bump 18 in one of the windows is measured. As will be recalled from FIG. 4, the image of each solder bump 18 inside of each bounding box 58 appears as an annulus. During step 59, the inner and outer diameter of the annulus within at least one of the bounding boxes 58 is measured, together with its brightness, its location and its topographical feature-shape (representing its circularity). While the values of these attributes for a single good solder bump 18 would suffice, it is desirable to measure the value of these attributes for each of a plurality of good solder bumps and then average the values as well as to calculate their standard deviation. The averages and the standard deviation for each attribute are thereafter stored in the vision processor 44 of FIG. 2.

Following step 59, the image of the chip carrier surface 13 (see FIG. 1) is captured under bright field illumination during step 60. During step 60, the ring light 40 of FIG. 2 is rendered inoperative while the light source 38 is energized, so that the surface 13 will be illuminated with the light beam 36. Next, a gray level threshold for the captured bright field image of the chip carrier surface 13 is established during step 62 just as the gray level threshold for the dark field image was set during 54. After step 62, then step 64 is executed, at which time a window 57 (see FIG. 6) is created about each row of solder bumps 18, and a bounding box 58 (see FIG. 6) is created about each bump within the window in exactly the same manner as during step 56. The same attributes calculated during step 56 are also calculated during step 64.

Upon completion of step 64, step 66 is executed and the same attributes measured during step 59 are again measured during step 66 while the chip carrier surface 13 is subjected to bright field illumination. Execution of the training routine ends (step 68) following step 66.

Figure 7:
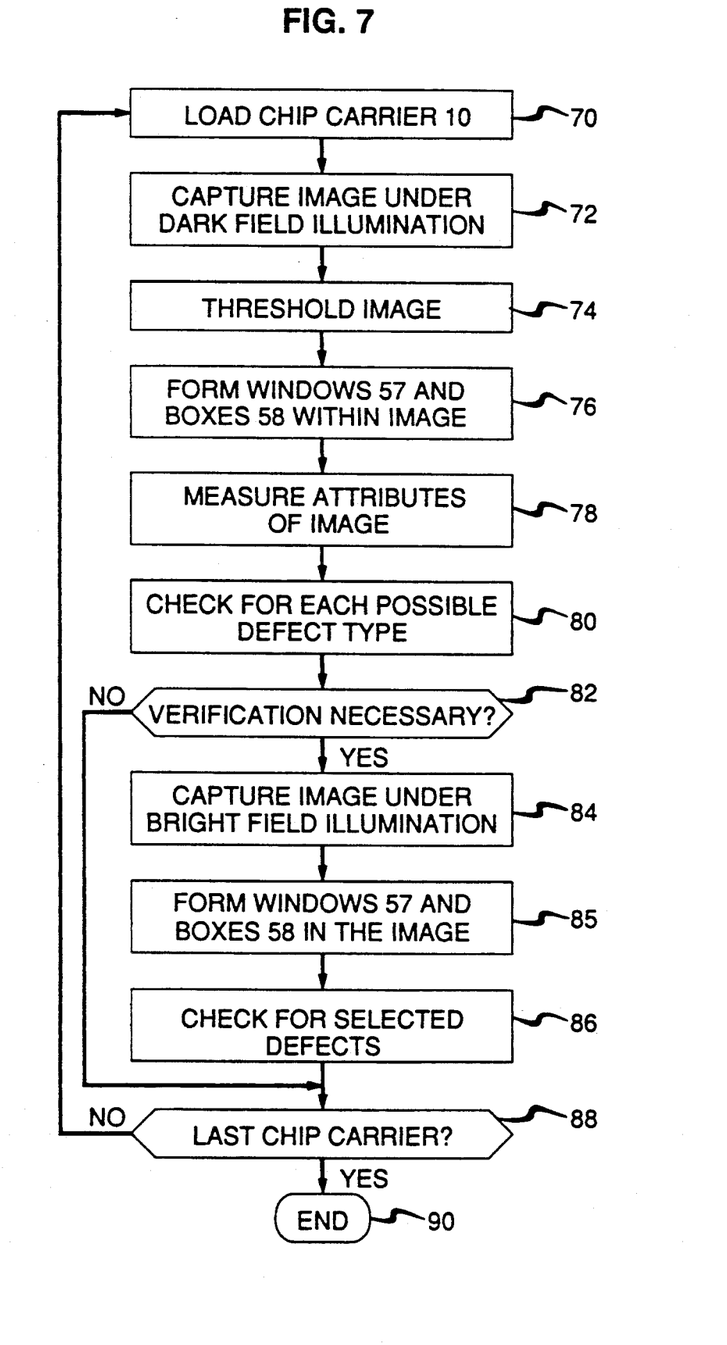
FIG. 7 is a flowchart diagram of a program executed by the system of FIG. 2 to inspect the chip carrier of FIG. 1.

Once the training routine of FIG. 5 has been executed to establish the average value and standard deviation for each of the above-described attributes in the image associated with a good chip carrier 10, then actual inspection of chip carriers of unknown quality may be commenced. Referring to FIG. 7, there is shown a flowchart representation of a program executed by the vision processor 44 of FIG. 2 to inspect a chip carrier of unknown quality. The "INSPECT" routine of FIG. 7 is initiated upon execution of step 70 whereupon a chip carrier 10 is loaded onto the stage 24 of FIG. 2. Next, the image of the chip carrier 10 under dark field illumination is captured (step 72). Following step 72, step 74 is executed, and the captured image is thresholded, that is to say, the portions of the captured image having a reflectance intensity below the threshold value set during step 54 of FIG. 5 are darkened. In this way, the bright areas in the captured image should correspond only to the bright features on the chip carrier surface 13, such as the solder bumps 18 (if any), any unbumped pads 14 of FIG. 1, and any solder spatter.

After step 74, step 76 is executed and a window 57 (see FIG. 6) is formed about each row of solder bumps 18, and a bounding box 58 is formed about each bright image within the window. Once the windows 57 and boxes 58 have been formed, then the same attributes measured during steps 56 and 59 of FIG. 5 are measured during step 78. In other words, the location and size of the windows 57 and the boxes 58 are measured, together with the brightness, the mean topographical feature-shape and inner and outer diameter of each annulus inside each box.

Once these attributes have been measured, a check is made during step 80 to determine whether any one of a set of specific defects is present. Each particular type of defect, such as a missing, squashed or bridged solder bump 18, or the presence of solder spatter, is ascertained by comparing a particular one of the attributes measured during step 78 of FIG. 7 to the corresponding attribute measured during one of the step 56 and 59 of FIG. 5. A missing solder bump 18 is detected by comparing the number of bounding boxes 58 found during step 78 to the number found during step 57 of FIG. 5 and by comparing the location of the boxes found during step 57 to that established during step 78. If the number of bounding boxes 58 found during step 78 is less, then one of the solder bumps 18 is probably missing, and accordingly, this type of defect is identified. A missing solder bump 18 is also indicated when the measured distance between bounding boxes 58 (corresponding to the distance between bumps) falls below a predetermined tolerance established from the standard deviation of the measured distance. If the number of measured boxes 58 found during step 78 exceeds the number found during step 57 of FIG. 5, then solder spatter is probably present.

A pair of solder bumps 18 which are defective because they are too closely spaced will be revealed when the actual location of the bumps (as established by the location of the bounding boxes 58) differs from their expected location by more than a predetermined tolerance related to the standard deviation of the measured distance. Alternatively, the same defect will be revealed when the measured distance between the solder bumps 18 (i.e., the measured distanced between the boxes 58) bumps exceeds a predetermined tolerance related to the standard deviation of the measured distance. Solder bumps 18 which are defective because there are "cold" (i.e., grainy or frosty) are indicated when the brightness of the annulus in each box 58 of FIG. 6 (representing the image of each solder bump) differs from the brightness measured during step 59 of FIG. 5 by a predetermined brightness tolerance which is established in accordance with the standard deviation of the measured brightness.

Should the outer diameter of the bright annulus inside each bounding box 58 of FIG. 6 be larger or smaller than the value measured during step 59 of FIG. 5 by more than a predetermined tolerance (established in accordance with the standard deviation of the outer diameter), then there is either excessive solder or poor wetting, respectively. If the mean topographical feature-shape measure of the annulus inside each bounding box 58 (representing its circularity) differs from the mean topographical feature-shape measure computed during step 59 of FIG. 5 by more than a predetermined tolerance (established from the standard deviation of this value), then the solder bump 18, represented by the annulus, is deemed defective because of surface deformations. For example, the bump 18 may be concave or elongated, giving rise to the difference between the actual and desired topographical feature-shape. When the inner diameter, but not the outer diameter, of the annulus inside a bounding box 58 is found to be greater than the value measured during step 59 of FIG. 5 by more than a predetermined tolerance established from the standard deviation of this value, then a squashed solder bump 18 is indicated. The relative magnitude of the inner diameter of the annulus inside the bounding box 58 is indicative of the height of the solder bump 18 represented the annulus so that the larger the inner diameter, the smaller the height of the bump.

Following step 80, then step 82 is executed, and a check is made to determine if it is necessary to verify if indeed a particular type of defect is present. In particular, if poor wetting, a near-short, a squashed solder bump 18, or solder spatter, is detected during step 78, verification of such defects is undertaken because such defects are the most difficult types to detect. Typically, verification is accomplished during step 82 by comparing whether the inner or outer diameter of the annulus in each bounding box 58 of FIG. 6 is less than or greater than, respectively, the value for that of a good solder bump 18.

If verification is deemed necessary during step 82, then step 84 is executed and the image of the surface 13 of the chip carrier 10 (both of FIG. 1) is then captured under bright field illumination. Next, step 85 is executed and a set of windows 57 and a set of bounding boxes 58 are created within the bright field image captured during step 84 in the same manner that the boxes and windows were formed during step 76. Following step 85, step 86 is executed, and a check is made to determine if the particular defects identified during step 80 under dark field illumination are present during bright field illumination.

To check whether a squashed bump 18 is indeed present, a comparison is made during step 86 as to whether the inner diameter of the annulus inside the bounding box 58, as measured during bright field illumination, is greater than the value measured during step 66 of FIG. 5. If so, then the solder bump 18 is indeed squashed, and this particular defect is confirmed. The presence of solder spatter is confirmed by comparing the number of bounding boxes 58 created during step 84 to the number established during step 66 of FIG. 5. If the number of boxes 58 created during step 84 is found to be greater, then solder spatter is indeed present. Poor wetting of the pads 14 of FIG. 1 is confirmed if the measured outer diameter of the annulus within the bounding box 58 containing the solder bump 18, previously found to exhibit poor wetting, is less than the value measured under bright field illumination during execution of the training routine of FIG. 5. A near short circuit, caused by two solder bumps 18 being too close to each other, is verified by comparing the location of the boxes measured during step 86 to the location measured during step 66.

It is entirely possible that poor wetting cannot be verified during step 86. The bright field image of the chip carrier surface 12 of FIG. 1 tends to be much richer in features, and therefore more difficult to analyze. For this reason, initial defect detection is completed using a high-content image with reduced complexity as is produced using dark field illumination. Bright field illumination is used only for verification. If the poor wetting is detected under dark field illumination during step 80, but not under bright field illumination during step 86, the vision processor 44 of FIG. 2 indicates this discrepancy.

Following step 86, or step 82 when no verification is required, step 88 is executed and a check is made to determine if the last chip carrier 10 of FIGS. 1 and 2 has been loaded on the stage 24 of FIG. 2. If so, then program execution ends (step 90). Otherwise, program execution branches back to step 70.

The foregoing describes a technique for detecting defective solder bumps 18 and solder spatter on a chip carrier 10 by capturing and thresholding the image and then creating a window 57 about each row of solder bumps, and a bounding box 58 about each bump. A set of predetermined attributes associated with the windows 57 and the boxes 58, as well as the image within each box, is measured and then compared to the corresponding attributes of a good chip carrier 10. A particular type of defect is revealed when a particular attribute differs from the corresponding attribute measured for a good chip carrier 10.

While the present technique has been described with respect to inspecting the solder bumps 18 on a chip carrier 10, it is equally useful for inspecting the solder bumps on a semiconductor wafer (not shown). In fact, the exact same apparatus 22 shown in FIG. 2 can be used; the only modification necessary is the addition of a wafer-handling mechanism as disclosed in my aforementioned article in the *AT&T Technical Journal*.

It is to be understood that the above-described embodiments are merely illustrative of the principles of the invention. Various modifications and changes may be made thereto by those skilled in the art which will embody the principles of the invention and fall within the spirit and scope thereof.

I claim:

1. A method for inspecting an article to detect missing and defective specular, topographical features on its surface and deformations in the topology of such features comprising the steps of:
    (a) illuminating the surface of the article with a first light directed at an acute angle to the surface from all of the sides thereof;
    (b) capturing the image of the surface;
    (c) creating a window within the image about each group of specular, topographical features and subsequently creating a bounding box about each topographical feature within each window;
    (d) measuring the value of each of a first predetermined set of attributes associated with the windows, the boxes within the windows, and the feature inside each box;
    (e) comparing the measured value of each first attribute to a separate one of a set of reference values, each representing the value of the corresponding first attribute when no defect, such as a missing or deformed feature, is present, and identifying the existence of a particular type of defect when the established value of a separate one of the first attributes differs from its associated reference value by more than a predetermined tolerance.

2. The method according to claim 1 further including the step of automatically confirming whether each of several particular types of defects is indeed present.

3. The method according to claim 2 wherein the confirmation step includes the steps of:
    (a) extinguishing the first light and directing a second light at the substrate to strike the surface substantially normal thereto;
    (b) capturing the image of the surface;
    (c) creating a window about each group of specular, topographical features, and subsequently creating a bounding box about each feature within each window;
    (d) measuring the value of each of a second set of predetermined attributes associated with the windows, the bounding boxes, and the feature inside each box; and
    (e) comparing the measured value of each second attribute to a separate one of a second set of reference values, each representing the value of a separate one of the second attributes when no defect is present, and verifying that a particular defect is indeed present when the measured value of the second attribute differs by more than a predetermined tolerance from the corresponding reference value.

4. The method according to claim 1 wherein the first set of predetermined attributes which are measured include: (a) the location, number and size of the windows; (b), the location, number and size of bounding boxes within each window, and (c), the shape, dimensions and brightness of the feature in each box.

5. The method according to claim 3 wherein the second set of predetermined attributes that are measured includes: (a) the number, location and size of bounding boxes within each window and (b) the shape, dimensions and brightness of the feature inside each box.

6. The method according to claim 1 wherein the specular, topographical features on the surface of the article are arranged in separate linear arrays and wherein a window is established within the image of the surface about each linear array of features.

7. The method according to claim 3 wherein the specular, topographical features on the surface of the article are arranged in separate linear arrays and wherein a window is established within the image of the surface about each linear array of features.

8. The method according to claim 1 wherein the reference values for each first attributes are obtained by performing steps (a)-(e) on an article known to have no defects.

9. The method according to claim 3 wherein the reference value for each second attribute is obtained by performing steps (a)-(e) on an article known to have no defects.

10. The method according to claim 1 wherein the specular, topographical features on the article comprise solder bumps.

11. Apparatus for inspecting an article having at least one solder bump on its surface to detect if the bump is missing or deformed, comprising:
   means for supporting an article;
   a first light source for illuminating the surface of the article with dark field illumination;
   image-acquisition means trained on the surface of the article normal to its plane for capturing the image thereof; and
   vision processing means coupled to the television camera for processing the output signal of the camera to detect a missing or deformed bump by (a) creating a window about each group of solder bumps and a bounding box about each feature within each window; (b) measuring the value of each of a set of predetermined attributes associated with the windows, the bounding boxes, and the solder bump inside each box; (c) comparing the measured value of each attribute to a separate one of a set of reference values, each representing the value of a separate one of the attributes; and (d) identifying each of a plurality of possible defects in accordance with such a comparison.

12. The apparatus according to claim 11 further including at least a second light source for illuminating the surface of the article with bright field illumination.

13. The method according to claim 10 further including the step of analyzing the topology of bumps to identify defects by examining the shape and intensity characteristics of bright contours representing the solder bumps.

* * * * *